(12) United States Patent
Klammler et al.

(10) Patent No.: US 7,284,448 B2
(45) Date of Patent: Oct. 23, 2007

(54) DEVICE AND METHOD FOR PASSIVELY MEASURING FLUID AND TARGET CHEMICAL MASS FLUXES IN NATURAL AND CONSTRUCTED NON-POROUS FLUID FLOW SYSTEM

(75) Inventors: Harald Rene Klammler, Steiermark (AT); Kirk Hatfield, Gainesville, FL (US); James William Jawitz, Gainesville, FL (US); Michael David Annable, Gainesville, FL (US); William George McDougal, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 61 days.

(21) Appl. No.: 10/989,617

(22) Filed: Nov. 16, 2004

(65) Prior Publication Data

US 2006/0101901 A1 May 18, 2006

(51) Int. Cl.
*G01F 1/74* (2006.01)
(52) U.S. Cl. .................................. 73/861.04
(58) Field of Classification Search .............. 73/861.04
See application file for complete search history.

(56) References Cited

U.S. PATENT DOCUMENTS

| | | | |
|---|---|---|---|
| 3,625,065 A * | 12/1971 | Thompson | 73/863.51 |
| 3,678,273 A | 7/1972 | Lewis | |
| 3,811,325 A | 5/1974 | Carter | |
| 3,993,131 A | 11/1976 | Riedel | |
| 4,107,525 A | 8/1978 | Hart, Jr. | |

(Continued)

FOREIGN PATENT DOCUMENTS

DE 42 30 919 A1 3/1994

(Continued)

OTHER PUBLICATIONS

Howard, Erik, "Direct Push Insitu Measurement of Groundwater and Contaminant Flux," Journal of Undergraduate Research—Aug. 2002, University Scolars Program—U. of Florida.

(Continued)

*Primary Examiner*—Robert Raevis
(74) *Attorney, Agent, or Firm*—McDonnell Boehnen Hulbert & Berghoff LLP

(57) ABSTRACT

An improved method and apparatus for simultaneously monitoring the fluid flux and the target chemical mass fluxes in fluid flow systems is provided comprising the use of a body or shell that is inserted into the flow field. Inside or outside this body is a bundle of one or more permeable sorptive columns. The extremes of each column are hydraulically connected to the outside flow field around the body of the device through a pair of small openings in the body. The known non-uniform flow velocity distribution around the body of the invention causes a pressure difference between pairs of openings used to connect internal or external column units. A preferred shape of the body is a hydrofoil. Alternatively, instantaneous measurement of the fluid flux and contaminant composition is possible using pressure transducers and a chemical sensor. The method of monitoring comprises placing the invention in contact with the contaminated flow field, thereby allowing target chemicals in the in the fluid to be transported through internal column units and be sorbed on the insoluble sorbent matrix. The permeable sorptive column unit is then removed and the sorptive matrix is analyzed directly or visually (if visible tracers are used) to determine cumulative fluid fluxes and cumulative target chemical mass fluxes.

3 Claims, 3 Drawing Sheets

U.S. PATENT DOCUMENTS

| | | | |
|---|---|---|---|
| 4,167,870 | A | 9/1979 | Haas |
| 4,484,626 | A | 11/1984 | Kerfoot et al. |
| 4,696,194 | A * | 9/1987 | Taylor ..................... 73/861.66 |
| 5,077,471 | A | 12/1991 | Smith, Jr. et al. |
| 5,134,890 | A | 8/1992 | Abrams |
| 5,290,528 | A * | 3/1994 | O'Connor et al. ............ 423/87 |
| 5,339,694 | A | 8/1994 | Looney et al. |
| 5,594,179 | A | 1/1997 | Marsh |
| 5,625,156 | A * | 4/1997 | Serrels et al. ............ 73/863.51 |
| 5,804,743 | A | 9/1998 | Vroblesky et al. |
| 5,821,864 | A | 10/1998 | Knop et al. |
| 5,833,388 | A | 11/1998 | Edwards et al. |
| 5,834,657 | A * | 11/1998 | Clawson et al. ......... 73/863.81 |
| 5,942,103 | A | 8/1999 | Wang et al. |
| 5,942,440 | A | 8/1999 | Dooley et al. |
| 6,118,519 | A | 9/2000 | Ipponmatsu et al. |
| 6,182,505 | B1 | 2/2001 | Segeral |
| 6,250,132 | B1 * | 6/2001 | Drzewiecki ................ 73/23.2 |
| 6,284,219 | B1 | 9/2001 | Ajami |
| 6,401,547 | B1 * | 6/2002 | Hatfield et al. .......... 73/861.04 |
| 6,666,081 | B1 * | 12/2003 | Babinsky et al. ........ 73/170.01 |
| 6,842,705 | B2 * | 1/2005 | Moriyama ................... 702/45 |

FOREIGN PATENT DOCUMENTS

| | | |
|---|---|---|
| EP | 0 763 731 A2 | 3/1997 |
| GB | 731 259 A | 6/1955 |
| GB | 2 144 214 A | 2/1985 |
| JP | 408334396 A | 12/1996 |
| WO | WO/97/48971 | 6/1997 |
| WO | PCT WO97/46853 | 12/1997 |
| WO | PCT/US00/28655 | 10/2000 |
| WO | WO/03/098167 A | 11/2003 |

OTHER PUBLICATIONS

University of Florida—Office of Technology Transfer, "A Device and Method for Measuring Fluid and Solute Fluxes in Flow Systems," flyer seeking partner to license, no date.

Gupta, Ram S. Ph.D., P.E., 2001."Hydrology and Hydraulic Systems" Second Edition, Waveland Press, Inc.Chapters 6 and 10; pp. 266-307; 539-543.

Tietjens, O.G., Ph.D. 1934. Applied Hydro- and Aeromechanics; Engineering Societies Library, NY; Dover Publications, NY; Chapters IV, VII, pp. 58-85; 226-231.

Tietjens, O.G., Ph.D. 1934. Fundamentals of Hydro- and Aeromechanics; Engineering Societies Library, NY; Dover Publications, NY; Chapters IX and X; pp. 107-188.

Crabtree, R.W. and Kirkby, M.J.; "Ion-Exchange Resin Samplers for the In Situ Measurement of Major Cations in Soilwater Solute Flux;" Journal of Hydrology, 80 (1985) 325-335; 1986.

Ballestero et al., "Monitoring and Sampling the Vadose Zone;" Practical Handbook of Ground-Water Monitoring; Lewis Publishers. pp. 97-141, no date.

Wagenet, R.J.; "Water and Solute Flux;" Methods of Soli Analysis Part 1-Physical and Mineralogical Methods Second Ed.; No. 9-Agronomy 1986; pp. 1055-1088.

Dalton et al.; "Acquisition and Interpretation of Water-Level Data;" Practical Handbook of Ground-Water Monitoring; Lewis Publishers; pp. 367-395, no date.

Sevee, John; "Methods and Procedures for Defining Aquifer Parameters;" Practical Handbook of Ground-Water Monitoring; Lewis Publishers; pp. 397-447.

Betz, Albert; Konforme Abbildung—springer-Verlag; Berlin/Gottingen/Heidelberg, 1964; pp. 100-223. (No translation available).

S. F. Thornton; S.E. Oswald (EDS): "Groundwater Quality: Natural and Enhanced Restoration of Groundwater Pollution" 2002, IAHS Press, XP008065362 ISBN: 1901502864, pp. 25-31.

Partial International Search Report for Application No. PCT/US2005/041585.

International Search Report for Application No. PCT/US2005/041585.

* cited by examiner

DEVICE AND METHOD FOR PASSIVELY MEASURING FLUID AND TARGET CHEMICAL MASS FLUXES IN NATURAL AND CONSTRUCTED NON-POROUS FLUID FLOW SYSTEM

BACKGROUND OF THE INVENTION

1. Field of the Invention

The present invention generally relates to the detection of organic and inorganic dissolved or gaseous substances in fluids, and, in particular, to the analysis of fluid flow systems for the characterization and quantification of organic and inorganic dissolved or gaseous substances therein. More particularly, this invention relates to devices and methods for measuring cumulative mass fluxes of organic and inorganic dissolved or gaseous substances and cumulative fluid fluxes in fluid flow systems. The term fluid as used herein encompasses any type of liquid or gaseous media (e.g. water or air) containing or not one or more organic and/or inorganic dissolved or gaseous substances (e.g. contaminants or nutrients), while the term flow systems as used herein includes, but is not limited to, constructed flow systems such as closed conduits (e.g. pipes, sewers, vents, stacks, or chimneys) or open conduits (e.g. aqueducts, canals, ditches, rivers, or streams), and natural flow systems (e.g. natural water bodies such as estuaries, lakes, wetlands, and oceans). The term target chemical as used herein encompass dissolved inorganic and organic chemicals and inorganic and organic gases present in the fluid and these target chemicals may include contaminants, pollutants, and nutrients. However, as opposed to our earlier issued U.S. Pat. No. 6,401,547, which describes an approach to determining cumulative fluid fluxes and cumulative target chemical mass fluxes through porous media (pressure potential flow), the herein presented invention aims at applications that complement the before mentioned patent to non-porous fluid flow systems (velocity potential flow).

2. Description of the Relevant Art

The presence and transport of target chemicals in fluid flow systems can present significant pollution problems to nature and society and can be of great importance to industrial processes. For example, as to surface water supplies or other water resources (short: water flow systems), a wide variety of organic and inorganic target chemicals may be present in this particular type of flow system depending on how contiguous lands drained by or feeding said flow systems have been used and if said fluid flow systems receive contaminated water derived from external sources (e.g., septic systems, drainage tiles, industrial and municipal outfalls etc.). Many different organic and inorganic compounds (e.g., non-halogenated and halogenated organic compounds) may exist in water flow systems adjacent to factory sites, agricultural lands, military bases, urban areas, and other locations where extensive use of these chemicals has occurred over long time periods or accidental spills or inappropriate disposal have occurred. Of particular concern are pesticides, endocrine disrupters, halogenated (e.g., chlorinated) solvents including perchloroethene (PCE), trichloroethene (TCE), dichloroethane (DCA), vinyl chloride (VC), methylene chloride (MC), and others. However, in addition to the above organic compounds, a wide variety of other organic compounds shall be encompassed within the term "organic contaminants" as discussed below. Of equal concern is the presence of benzene, toluene, xylenes, and other constituents of petroleum-based fuels (e.g., jet fuel, gasoline, diesel fuel, and the like) in waste-bearing geologic formations underlying various transportation-related facilities. Examples of such facilities include gasoline stations, airports, military bases, and the like. Other contaminants include various pesticides and inorganic/organic nutrients used in crop production or suburban lawns and gardens or golf courses; and trace metals such as arsenic and chromium and the like used in industrial operations. At many sites, both organic and inorganic contaminants may be found as mixtures. A contaminant group designated as polyaromatic hydrocarbons (PAHs), such as naphthalene, phenanthene, anthracene, benzo-a-pyrene and others, are constituents of coal and/or tars and creosote found at former gas manufacturing sites and wood treating facilities. Regardless of the particular target chemicals of concern, the presence of these chemicals in water flow systems, as illustrated in this example, is a considerable public health concern and of ecological significance. As this example furthermore demonstrates, the present invention shall not be restricted to the monitoring of any given organic or inorganic compounds.

In general, several methods have been used to analyze fluids (and in particular water) for dissolved compounds and to quantify flows (fluxes integrated over transect areas) in fluid flow systems. In fact, our earlier issued U.S. Pat. No. 6,401,547 describes an approach to determining cumulative liquid fluxes and cumulative target chemical mass fluxes through porous media. Other examples involving direct methods for measuring fluid discharges include: acoustic or electromagnetic methods, and methods based on direct measurements of local flow velocities (fluid fluxes), e.g., using current meters to measure local fluxes, in a stream for the purpose of calculating depth integrated stream discharges using some standard method (e.g. two-point method, integrated measurement method, etc.). More examples that are potentially related to water flow systems are: tracer dilution methods (sudden or constant injection), as well as methods based on the deployment of hydraulic devices (e.g. weirs or notches). Furthermore, water discharges can be measured indirectly through monitoring the stage of a stream and inferring the discharge from a known stage-discharge relationship. Descriptions of all these methods are widely available in hydrology literature.

Measurements of target chemical mass discharges are generally performed by taking fluid samples at discrete moments in time and at discrete locations over transects. The fluid samples are analyzed for concentrations of target chemicals and the resultant mass fluxes calculated as the product of the target chemical concentrations and the measured or estimated fluid fluxes (velocities). Often is the case that short-term concentrated sampling events are conducted to generate a time-series of measurements from some peak event (e.g. a storm or spill). Hundreds of fluid samples may be collected and processed for the purpose of estimating related cumulative mass loads of target chemicals (target chemical mass fluxes integrated over a transect area) transported in a fluid flow system. From the nature of most of the methods mentioned it can be observed that fluid discharges are only measured at discrete points in time and that cumulative or time averaged discharges have to be obtained from interpolating and integrating of recorded data time series. The same applies to the measurement of the mass discharges of target chemical, which, in addition, are only indirectly obtained from concentration and fluid flux data. Hence, the measurement of cumulative or time averaged fluid and target chemical mass discharges can be performed with current methods, yet the technical requirements in the field for data transmission and logging are considerable and for target chemical mass discharge additional computations are required to arrive at final flux estimates.

While the prior methods provide important information regarding the levels of contamination in fluid flow systems of concern, they do not allow direct measurements of target chemical mass fluxes. And although prior methods and apparatus are capable of measuring instantaneous fluid fluxes, most do not allow direct measurements of cumulative fluid fluxes. Finally, the commonly used methods that exist do not permit simultaneous measurements of target chemical cumulative mass fluxes and cumulative fluid fluxes.

Current methods for estimating the target-chemical mass flux ($J_{sol}$) in fluid flow systems are made from independent instantaneous point measurements of fluid flux ($v_o$) and target chemical concentration (C) in sampled fluids. Several methods exist for measuring $v_o$ and C in fluid flow systems, and all provide measures at discrete moments in space and time. However, no single method exists for non-porous fluid flow systems that samples $v_o$ and C at coincident points in space and time and no method exists to measure cumulative target chemical mass flux and cumulative fluid flux. Measured $v_o$ and C are used as shown in the following equation to estimate the instantaneous target chemical mass flux, J.

$$J_{sol} = v_o C \quad (1)$$

Equation (1) is assumed to characterize target chemical mass flux at a point in space or over a specified sampling dimensions (i.e., an area perpendicular to the direction of fluid flow) and for a reported sampling time. For dynamic fluid flow systems, this approach of characterizing target chemical mass flux is subject to significant experimental and conceptual errors. Consider first, that the fluid flux, $v_o$ and the target chemical concentration, C are both functions of position and time. This suggests that the magnitude of the target chemical mass flux, $J_{sol}$, also varies with position and time. Thus, any sampling of $v_o$ and C that does not occur at coincident points in space and time precludes accurate local estimation of the magnitude of both fluid and target chemical mass fluxes. Second, the short-term sampling procedures often used to obtain C and $v_o$ preclude estimation of the time-integrated (i.e., cumulative) values for fluid flux and target chemical mass flux. Such time-integrated target chemical mass fluxes are useful for assessing health risks associated with contamination found in water or air flow systems, for example, such as for assessing contaminant loads generated within watersheds or along stream and river reaches, for assessing the total amount of off-site contamination contributed by one or more sources, and for assessing the benefits of removing or remediating sources of contamination. Moreover, the inherent time integration of both fluid flux and especially target chemical mass flux at sampling points performed by the invention allow for the quantification of target chemical mass loads that can not be measured by traditional concentration sampling any more if the target chemical concentrations are below the detection limit of the applied technology. However, target chemical mass loads may still be considerable, even for very high degrees of dilution if the fluid discharge is high enough. In addition, the time integration of measured fluid flux and target chemical mass flux eliminates the risk of not detecting some peak event (e.g. storm or spill) as it may be the case with time-discrete flux and concentration sampling.

Traditional testing methods also require a large amount of expensive equipment, are labor intensive, and involve complex operating procedures. Moreover, conventional monitoring techniques which require the removal of numerous fluid samples for individual testing typically generate large quantities of waste products (e.g., residual sample materials) that, if sufficiently contaminated or hazardous by their nature, can present significant disposal problems. Prior to the development of the present invention, a need therefore remained for an efficient testing system which avoids these disadvantages and enables fluid flow systems to be tested in an accurate, rapid, and effective manner.

The claimed invention represents a unique and highly-efficient alternative to the methods listed above. It does not require extensive equipment (e.g., pumps) and complex operating procedures. The invented device can be used to analyze large fluid flow systems without extracting any contaminated fluid sample materials so that problems with disposal of generated waste fluids are avoided. The invented device can be used to obtain cumulative estimates of the magnitude of both fluid and target chemical mass fluxes at specified point locations over the two dimensions of a transect that is oriented perpendicular to the direction of flow in the flow system. Alternatively, it can be used to provide instantaneous analysis of the flow system through the use of electronic pressure transducers and chemical sensors. The instantaneous information can be obtained alone or in combination with the cumulative analysis. Finally, the method and apparatus described below enable the fluid flow system of interest to be analyzed at multiple locations simultaneously so that target chemical mass loadings to the flow system may be "mapped" and thus, enabling, for example, the delineation of locations of concern such as target chemical sources (e.g. certain watershed areas, stream segments, water bodies etc.). Decontamination of water flow systems, for example, can then occur in a more site-specific and accurate manner. The present invention therefore involves a highly effective testing system which represents a substantial advance in the art of target chemical (e.g., nutrient or contaminant) detection, target chemical source delineation, and remediation of, in particular, water flow systems as discussed further below.

However, according to the initial definition of the term "fluid" as used herein, the potential applications of the invention shall not be restricted by any means to the example given above, which uses water as a fluid in order to be most illustrative. Other examples for potential applications include point source identification of air pollution (e.g. industrial plants), quality control of fluids required in industrial processes (e.g. purity or chemical composition of liquids).

SUMMARY OF INVENTION

It is an object of the present invention to provide a highly efficient testing method and apparatus which enables the quantitative and qualitative analysis of target chemicals in fluid flow systems.

It is another object of the invention to provide a method and a device for capturing a representative sample of target chemicals in a fluid flow system which allows the analysis of a wide variety of different organic and inorganic chemicals at varying levels.

It is another object of the invention to provide a method and a device for the measurement of significant target chemical mass loads where chemical concentrations are highly diluted but the fluid discharge is large It is another object of the invention to provide a method and a device for eliminating the risk of not detecting short time (peak) events between sampling events.

It is another object of the invention to provide a method and apparatus for monitoring target chemicals in fluid flow systems, which uses an operating system and procedure of minimal complexity.

It is another object of the invention to provide a method and apparatus for monitoring target chemicals in fluid flow systems, which avoids the need for pump systems.

It is a further object of the invention to provide a method and apparatus for monitoring target chemicals in fluid flow systems, which enables testing to take place without physically removing any fluid samples from the test area.

It is an even further object of the invention to provide a method and apparatus for monitoring target chemicals in fluid flow systems, which avoids the generation of waste products (e.g., residual sample materials), and likewise eliminates the disposal problems associated therewith.

Another object of the invention is to provide a method and apparatus for monitoring target chemicals in fluid flow systems, which is characterized by reduced labor requirements and processing times.

It is a still further object of the invention to provide a method and apparatus for monitoring target chemicals in fluid flow systems, which enables a spatial distribution (e.g., a vertical or horizontal analysis) of the chemical mass fluxes and fluid flux to be obtained simultaneously.

It is a still further object of the invention to provide a method and apparatus for monitoring fluids and target chemicals and their associated local fluxes in fluid flow systems, which facilitates the mapping of target chemical mass loadings along the reach of a fluid flow system in a highly effective manner so that, in the case of contaminated water flow systems for example, site-specific, high-efficiency remediation or pollution control measures may be initiated.

It is a still further object of the invention to provide a method and apparatus for monitoring fluids and target chemicals and their associated local fluxes in fluid flow systems to facilitate an assessment of the magnitude of target chemical mass flow and fluid flow leaving a source (e.g. watershed, industrial plant) or compliance boundary.

It is a still further object of the invention to provide a method and apparatus for monitoring fluids and target chemicals and their associated local fluxes in fluid flow systems to facilitate, for example, an assessment of the total amount of off-site contamination and contaminant loading contributed by one or more point and nonpoint sources.

Another object of the invention is to provide a device and method for measuring the following at specific locations in fluid flow systems:

1) Magnitudes of local cumulative fluid fluxes, and
2) Magnitudes of local cumulative mass fluxes of target chemicals associated with fluid flows.

In accordance with the foregoing, the invention involves both a system and a method that uses a device designed to simultaneously measure local cumulative fluxes of target chemicals and cumulative fluid fluxes when placed within a fluid flow systems. As used herein, "flow system" can be, but is not limited to, surface waters, air, or other fluids flowing enclosed as pressurized pipes or in open systems such as, sewers, wetlands, rivers, streams, canals, estuaries, oceans, vents, stacks, and chimneys. Typically, fluids within flow systems contain target chemicals, including organic and/or inorganic solutes or gases of concern.

The monitoring device of the present invention is comprised of two major components: (1) a body or shell (e.g. hydrofoil) that is inserted into the flow field, and (2) a bundle of one or more permeable sorptive columns that are located inside or outside the body of the device in a way that they do not disturb the flow field of the fluid around the device. The extremes of each column are hydraulically connected to the flow field around the body of the device through a pair of small openings in the shell of the unit. For each column, one of the openings allows fluid from outside the body to flow passively into the column while the other functions as an outlet to discharge captured fluid; hence, the invention functions to passively intercept fluid from outside the body or shell, it allows this fluid to flow through a connected sorptive column unit, and then discharges the intercepted fluid back into the surrounding flow field.

The sorptive column unit contains at least one matrix of hydrophobic and/or hydrophilic permeable and insoluble sorbents that are capable of retaining organic and/or inorganic target chemicals present in the fluid intercepted by the invention. The sorbing matrix can also be impregnated with known amounts of fluid-soluble tracers; these tracers are used to estimate total fluid flux in the flow field adjacent to the body of the invention. The selection of sorbent matrices to be in the column units could be, but need not be limited to porous pellets, fibers, or stabilized liquids or gels. The sorbent matrix or matrices are packed in one or more columns, which are positioned inside or outside the body or shell of the claimed invention without disturbing the flow field of the fluid around the device. These sorbents could have the inherent capacity to selectively sorb target chemicals from the fluid intercepted by the invention or in the alternative, the matrix can be coated or impregnated with specific sorbents that are selected to absorb or adsorb target chemicals.

DETAILED DESCRIPTION

Figure 1:
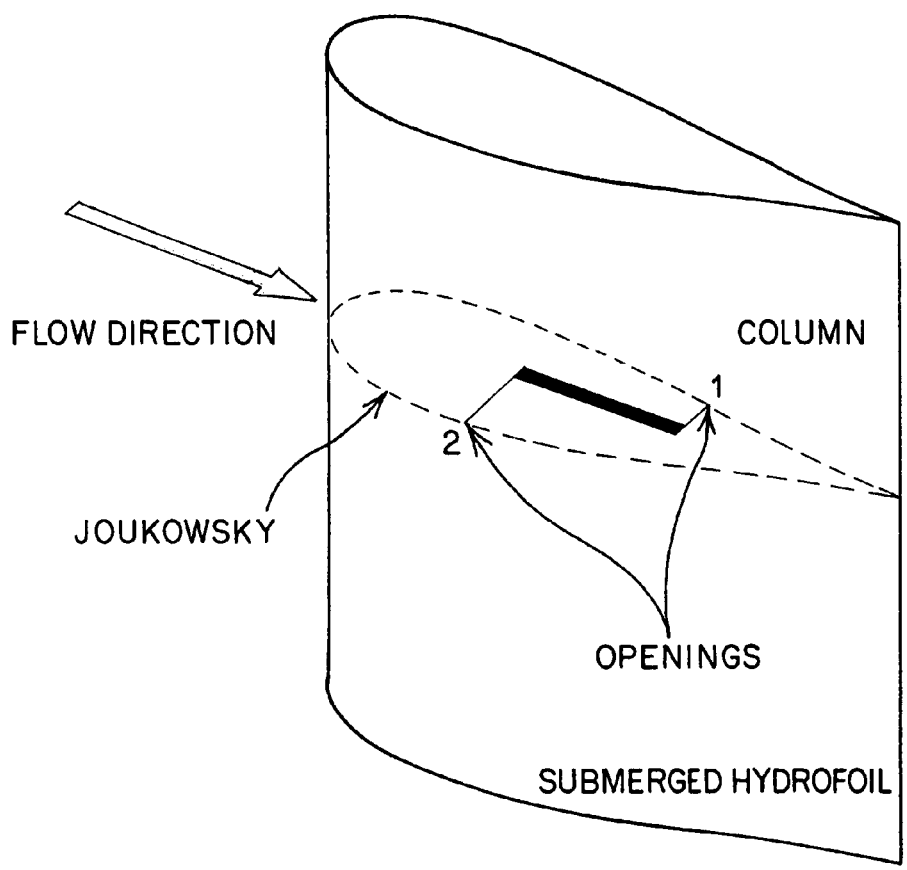
FIG. 1 shows a submerged device comprised of body or shell shaped like hydrofoil with a sorptive column installed inside the body and with the extremes of the column hydraulically connected to the flow field outside the body through a pair small openings in the shell.
Figure 2:
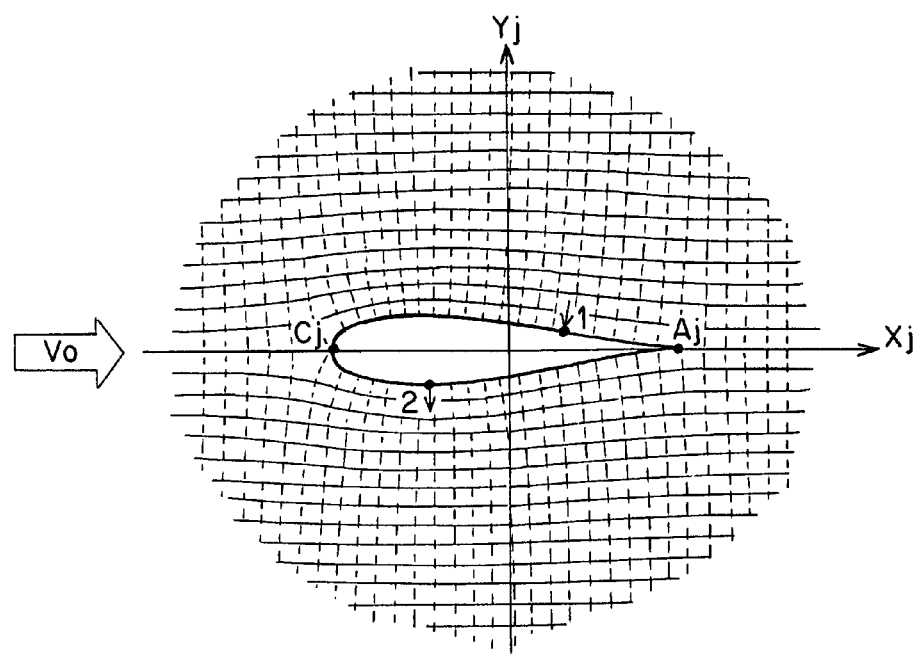
FIG. 2 shows a cross-sectional view of the device and of the flow around the device, where the shape of device represents a symmetric Joukowsky profile with a shape parameter b=0.85. This view is shown in the $z_j$ complex plane with numbers 1 and 2 indicating the locations of two openings that permit fluid to enter and exit the body of the device.

The claimed invention is designed to simultaneously measure cumulative or time averaged fluid and target chemical mass fluxes in fluid flow systems as defined above. The device is comprised of two major components, a body or shell that is inserted into the flow field, and a bundle of one or more permeable sorptive columns positioned inside or outside the body of the device without disturbing the flow field of the fluid around the device. The extremes of each column are hydraulically connected to the outside flow field around the body of the device through a pair of small openings in the body as illustrated in FIG. 1. The known non-uniform flow velocity distribution around the body of the invention causes a pressure difference between pairs of openings used to connect internal column units. In general each pair of openings is located in the same cross section of the body (e.g., at equal depths below the water surface if the device is installed vertically), and on opposite sides of the profile but never directly across from each other in the case of symmetric profiles. This is shown in FIG. 2. The pressure difference between paired openings generates a pressure gradient within the internal sorptive column. The column initially contains known amounts (masses) of one or more resident tracers, which are gradually eluted by the flow through the column due to the pressure gradient. By determining the mass of each tracer remaining in the column after exposing the invention to a flow field and knowing the relationship between the magnitude of the flow through the column and the fluid flux in the fluid flow system, the cumulative (or time averaged) fluid flux in the fluid flow systems can be estimated. Furthermore, the sorptive media in the column also retains dissolved or gaseous target chemicals in the fluid passed through the column, which allows for estimating the cumulative (or time averaged) target chemical mass flux from the amount of target chemical detected in the column after exposing the invention to the flow field.

The column component of this invention contains at least one insoluble matrix of various hydrophobic and hydrophilic sorbents that have the property to selectively adsorb or absorb organic and inorganic target chemicals (e.g., contaminants) present in a fluid flowing through the device.

The sorptive matrix inside each column unit contains at least one sorbed resident tracer. The column unit may consist of a hollow tube or like structure suitable to hold the insoluble matrix. As stated, the insoluble matrix can take the form of particles, such as pellets, aggregates, spheres or other geometric forms. The column unit is designed so that it can be introduced and removed from the body of the invention. The matrix must be insoluble when placed in the flow of the fluids of interest, and preferably is comprised of both adsorbents or ion exchange media. Adsorbents can be selected from aluminas, silicates, aluminosilicates (including molecular sieves), silica gel, magnesium or calcium silicate, clays, carbons and organic polymers. If the matrix comprises ion exchange media, it can comprise cation and anion exchangers, gel resins, phenolic resins, sulfonated phenolic resins, polymer cellulose composites and zeolites.

The target chemical mass retained on the sorbent matrix contained in the unit can be used to estimate cumulative target chemical mass fluxes and time-average target chemical mass fluxes. These flux measurements are valid at the locations of the front extremes of the cross sections of the device that contain the small openings in the body for fluid intake and outlet for each column.

As mentioned, the insoluble sorbent matrix contained within the unit also is impregnated with known amounts of one or more resident fluid-soluble tracers. Preferably these resident tracers comprise organic and inorganic compounds with a range of partitioning characteristics. Examples of hydrophobic species which might be used as tracers include branched and straight-chain aliphatic hydrocarbons, aliphatic alcohols, aromatics and poly-aromatic hydrocarbons (PAHs), and non-ionic surfactants. Anionic tracers can include benzoates, benzenesulfonates, phenates, aliphatic carboxylic acids, and inorganics such as halides, nitrates, nitrites, sulfates, sulfites, phosphates, and metal oxides. Cationic tracers can include ammonium, organic amines, heterocyclic compounds, and inorganic metal ions. The tracers are selected based on the expected or known fluid and target chemicals to be monitored and measured. For example, if perchloroethylene is known to be a contaminant in water, then a tracer selected from the group consisting of methyl-substituted alcohols such as methanol, 2-methyl-2-pentanol and 4,2-dimethyl-3 pentanol, would be used. Likewise, if chromate is known to be a contaminant in water, then a tracer selected from the group consisting of inorganic or organic anionic tracers is used. Alternatively, if nitrate is known to be a contaminant in water, bromide might be elected as a tracer used on an anion exchange resin media. These tracers are used to estimate total fluid flux. As fluid flows through each column unit, soluble or volatile (in the case of gases fluids) tracers will be leached from the sorbing matrix and lost from each column unit.

One significant potential application of the invention will be the measurement of cumulative contaminant mass fluxes in streams. In this application the invention containing at least one column unit filled with an insoluble sorbing matrix having one or more tracers impregnated thereon is installed in a stream or river. Solutes from a small fraction of the total volume of flow around the body of the invention are retained on the sorbing matrix in the column under natural hydraulic gradients generated from the pressure distribution around the body of the invention. The invention is allowed to remain at a desired location within the stream for a fixed period of time, and then the column unit(s) are removed to permit laboratory analysis of the sorbent for adsorbed contaminants and the above-described tracers to permit characterization (magnitude) of both cumulative water flux and cumulative contaminant flux.

Continuing with the above example of an application of the invention in a stream, it is the result of having surface water flowing around the body of the invention over time, that cumulative flow and the cumulative horizontal solute flux can be measured. For the same invention designed to interrogate the entire vertical depth of a stream or river, multiple intake ports at various depths at a verically installed deivce connected to multiple column units would yield a vertical characterization of the horizontal cumulative fluid flow distribution and the horizontal cumulative contaminant flux distribution. In addition, this device would provide a vertical distribution of contaminant fluxes. The claimed invention is placed in a monitoring location, and subjected to fluid flux for a specific time period and then the internal columns are removed from the shell or body of the device. To quantify the cumulative fluid flux the displacement of visible resident tracers on the sorptive column can be used; otherwise, the matrix is then removed from the column unit for direct analysis of residual tracer masses and retained contaminant mass. The analysis involves, extracting the retained solutes and remaining tracer(s), performing analysis of extracted materials and calculation of magnitudes of cumulative or time-averaged fluid and solute mass fluxes. If the columns are equipped with chemical sensors then it is possible to directly determine solute and tracer masses at a given point in time during the measurement and avoid the step of extracting solutes and tracers from the sorbent after the measurement period. An analysis of the sorbent material from multiple columns that reflect intake ports at various distances along the body of the invention (e.g. depths for vertical installations) quantifies (e.g. vertical) variations in the solute mass fluxes.

By installing several devices in a parallel manner along a control plane situated perpendicular to the general direction of fluid flow, it is possible to obtain local estimates of the cumulative solute mass fluxes over a matrix of points across a control plane. Vertical and horizontal characterization (cumulative and time-averaged magnitude), for example, of fluid and solute mass flow is possible by installing several units of the invention to ensure multiple measurements are taken over a transect that covers adequate horizontal and vertical distances in a plane perpendicular to the direction of fluid flow.

The physical principle that the claimed invention is based on is the creation of a difference in the static pressures between two points on the surface of the shell or body of invention when it is immersed in a fluid flow system. The shape of the body of the invention determines the properties of the nonuniform flow field around the body. Thus, spatial variations in both pressure and velocity occur along the surface of the device. Inside or outside the body is at least one column packed with permeable sorptive media. FIG. 1 illustrates a preferred shape shown as a symmetrical hydrofoil. The static pressure difference between two points on the body surface is used to induce a pressure gradient over the internal column unit, thus generating a flow through the column. For this purpose, the two extremes of the column are hydraulically connected to the outside flow field at the two points through small openings in the body of the invention where it is submerged in the fluid flow field. The column initially contains known amounts (masses) of one or more resident tracers, which are gradually eluted by the fluid flow through the column. By determining the amounts of each tracer remaining in the column after a period of exposing the invention to the fluid flow field, and by knowing the relationship between the magnitude of the flow through the column and the flow velocity of the fluid, the cumulative (or time averaged) fluid flux can be estimated. Furthermore, the sorptive media in the column also retains target chemicals in the fluid intercepted by the invention, which allows for estimating the cumulative (or time averaged) mass fluxes of target chemicals from the amount of each target chemical detected in the column after the measurement.

In theory, an unlimited number of shapes can be adopted for the body of the claimed invention; however, in order to achieve a well-defined pressure difference, streamlined body shapes are considered to be favorable, since they practically avoid the creation of a wake. In general, these streamlined shapes can be either two or three dimensional, and symmetric or asymmetric. Although many shapes will achieve the necessary pressure differential, preferred shapes include hydrofoils such as Joukowsky profiles, Karman-Trefftz profiles, and 2-dimensional Rankine bodies, or different kinds of drop shapes such as 3-dimensional Rankine bodies. The bluntness or slenderness of the profiles are adjusted to the expected flow velocities, i.e. for higher flow velocities a slender profile is applied, which still avoids the creation of a wake, while for lower flow velocities a blunt profile will still provide the required static pressure difference between the openings. A preferred shape is a symmetrical hydrofoil. It is also advantageous to largely avoid flow disturbances due to the presence of rods, for example, used to hold the streamlined bodies at a fixed position. For these reasons, it is seen to be convenient for applications in rivers or streams, for example, to design the submerged body as a hydrofoil that is vertically inserted into the stream flow as depicted in FIG. 1, such that it can monitor flow and target chemical fluxes over the whole stream depth. It is furthermore considered convenient to adopt a symmetric shape for the cross section rather than an asymmetric one, since it is not necessary to generate a lift force on the hydrofoil. By choosing the locations of the two openings (points 1 and 2 in FIG. 1) asymmetrically, the desired static pressure difference is obtained, even though the profile is symmetric. The body is fixed in place so as not to move longitudinally or laterally with the fluid flow, but is free to rotate around the vertical axis at (or close to) its upgradient (blunt) extreme. The symmetric profile ensures that the body will always be oriented parallel to the mean longitudinal flow direction, which may be of particular interest for applications with varying or reversing flow directions such as with tidal flows in estuaries, for example. Taking into account the above considerations, a symmetric Joukowsky profile is a convenient profile for the design of the invention cross-section.

FIG. 2 shows a cross-section view of one preferred embodiment of the invention body and of the flow around device, where the body shape is represented as a symmetric Joukowsky profile for b=0.85. This view is shown in the $z_j$ complex plane with numbers 1 and 2 indicating the locations of two openings that permit fluid to enter and exit the body of the device. The shape of the illustrated device varies with the value of b, a dimensionless parameter ranging from 0 (which defines a circle/blunt profile) to 1 (which defines a straight line/slender profile). The complex coordinates of any point $z_j$ located on the surface of the Joukowsky profile is determined using the following equation:

$$z_j = [z_c - (1-b)\cdot a] + \frac{(a\cdot b)^2}{[z_c - (1-b)\cdot a]} \qquad (2)$$

where $z_c$ is complex and defined as $z_c = ae^{i\alpha_c}$ over the range of $0 \leq \alpha_c \leq 2\pi$. The parameter a is determined by the total length c of the profile as $a=c(2-b)/4$ and does not affect the shape of the profile.

Given two points in the same cross sectional plane and on the surface of the invention body, the static pressure head difference between the two locations (j=1,2) is defined $\Delta\phi_{1,2}$ [L] and is calculated from the following equation (See FIG. 2 for a cross-section of the body of the invention):

$$\Delta\varphi_{1,2} = \frac{v_0}{2g}\cdot(\chi_2^2 - \chi_1^2) \qquad (3)$$

where $v_o$ [L/T] is the velocity or fluid flux of the undisturbed ambient flow field; g [L/T$^2$] is the acceleration of gravity, $\chi_j$(j=1,2) is the dimensionless ratio of the fluid flux at location j to the ambient fluid flux $v_o$. The value of $\chi_j$ is calculated from the following equation:

$$\chi_j = \frac{\left|1 - \frac{a^2}{z_c^2}\right|}{\left|1 - \frac{(a\cdot b)^2}{[z_c - (1-b)\cdot a]^2}\right|} \qquad (4)$$

Figure 3:
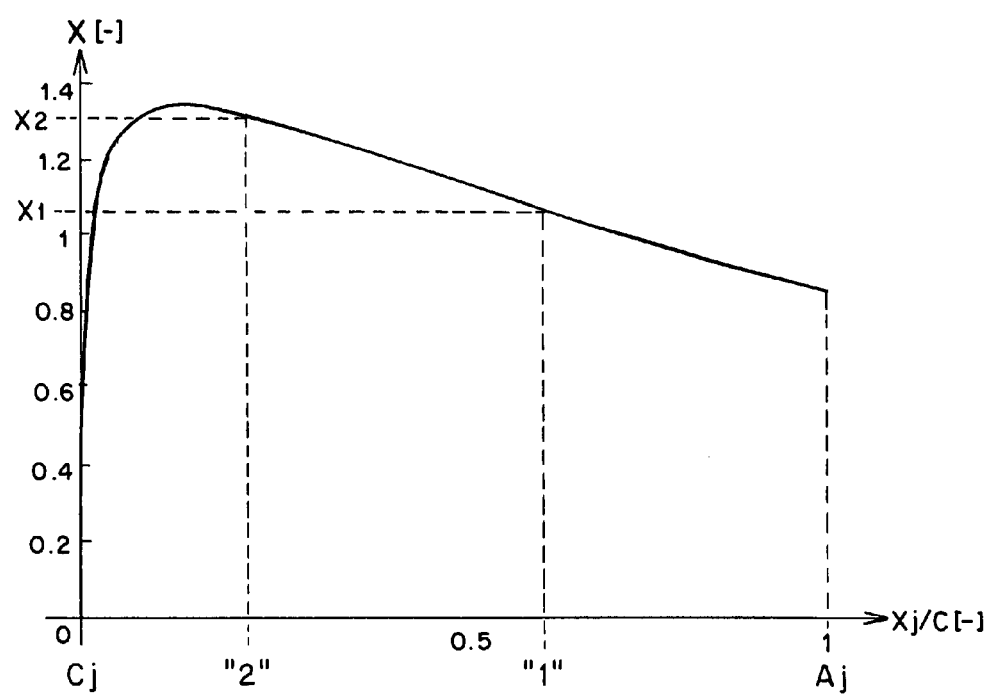
FIG. 3 shows a plot of values of $\chi[-]$ along the major principal axis of the device's cross section where the assumed shape is a symmetric Joukowsky profile for b=0.85. Also shown are the values for $\chi_j$ (j=1,2) for the two openings that permit fluid to enter and exit the body of the invention.

FIG. 3 illustrates a plot of X along the $\chi_j$ axis (which is oriented in the direction of flow) of a device shell possessing the same Joukowsky profile illustrated in FIG. 2; where it is assumed that b=0.85, which translates into a width to length ratio of the profile of approximately 0.2. The length c of the profile in FIG. 3 has been normalized to unity to emphasize the fact that the velocity distribution outside and along the profile is invariant with the absolute size of the profile. However, the actual physical size of a profile is chosen to be sufficiently big with respect to the scale of expected flow non-uniformities in order to reduce their effects on the measurement. For example, with applications in rivers or streams suggested values for c may range in the higher submeter of lower meter scale, while other applications (e.g. pipeflow) may require (and allow for) smaller profiles.

A sorptive column, hydraulically connected to the outside flow field around the invention body, initially contains known amounts of one or more resident tracers, which are gradually eluted by the flow through the column due to the higher pressure gradient. By determining the amount of tracer remaining in the column after a period of exposing the invention to the flow field and knowing the relationship between the magnitude of the flow through the column and the ambient fluid flux $v_o$ (e.g., of the stream), the cumulative (or time averaged) flux can be estimated in fluid flow systems.

$$v_0 = \sqrt{\frac{2g}{\chi_2^2 - \chi_1^2} \cdot \frac{L^2 \theta R_{d,tr}}{k_f t_m} \cdot (1 - m_{tr,r})} \quad (5)$$

where $k_f$ [L/T] is the hydraulic conductivity of the permeable sorptive media in the column; $t_m$ [T] is the duration that the invention was exposed to the flow field; L [L] is the length of the column;. $m_{tr,r}$ [–] is the relative mass of resident tracer remaining in the column after sample time $t_m$ [T]; θ [–] is the relative fluid content in the column; and $R_{d,tr}$ [–] is the retardation factor of the tracer associated with the fluid and the sorbent media packed in the column.

Finally, the sorptive media packed in the column may be selected to intercept and retain specific target chemicals such as dissolved contaminants or gases in the monitored flow field. From the mass of each target chemical detected in the column after the measurement period $t_m$, an estimate can be made of the cumulative (or time averaged) target chemical mass flux.

$$J_{sol} = \frac{2gL}{Ak_f(\chi_2^2 - \chi_1^2)} \cdot \frac{m_{sol}}{t_m v_0} \quad (6)$$

where $J_{sol}$ [M/L$^2$T] is the time-averaged target chemical mass flux; $m_{sol}$ [M] is the mass of target chemical sorbed on the column as determined from quantitative analysis of the sorptive media or by embedded chemical sensors; and A [L$^2$] is the cross sectional area of the column.

Another embodiment of the invention allows for the instantaneous measurement of the fluid flux properties, including target chemical identification and concentration. The instantaneous monitoring feature is accomplished by the use of pressure transducers and chemical sensors located on the shell that can measure the pressure differential and analyze the chemical composition of the fluid flowing around the shell, respectively. The specific designs of the pressure transducers and chemical sensor are not critical to the invention as long as they do not significantly change the shape of the surface of the submerged shell, can withstand submerged conditions and transmit pressure and chemical data electronically in real time so as to allow instantaneous determination of the fluid flux and concentrations of target chemicals. The pressure transducers and chemical sensors can be used alone (FIG. 1 at points 3 and 4 show one possible location of these sensors, respectively, as coinciding with the location of the surface parts) on the shell or in addition to the bundle of sorptive columns inside the shell as described above. Communication of the pressure and chemical data can be made using hardwired connections to the shell or transmitted wirelessly using conventional wireless technology such as Bluetooth or WiFi.(IEEE 802.11).

As previously discussed, the present invention offers numerous benefits and advantages including (1) the simultaneous measurement of both cumulative fluid and target chemical mass fluxes; (2) the simultaneous long and short-term measurement of both cumulative fluid and target chemical mass fluxes providing the ability to measure highly diluted chemical mass loads and eliminating the risk of not detecting peak events (3) the rapid and efficient testing of water supplies using a minimal amount of energy, equipment, and process steps, with the elimination of complex procedures involving pumps, (4) the ability to test a wide variety of water samples and supplied in situ for many different target chemicals; (5) elimination of the need to physically withdraw multiple fluid samples at the test site which eliminates waste accumulation and disposal problems; (6) a high degree of portability which enables testing to occur at remote locations without transporting large amounts of equipment; (7) a reduction in equipment, material, and personnel costs compared with traditional procedures; (8) the ability to test fluid flow systems (both atmospheric and water), for target chemical loads generated within watersheds or along stream and river reaches; (9) the ability to assess off-site contamination contributed by one or more sources; and (10) the ability to assess the benefits of removing or remediating sources of contamination.

For these reasons, the claimed invention represents a significant advance in the art of solute and, in particular, pollution detection and control in fluid flow systems. Having herein set forth preferred embodiments of the invention, it is anticipated that suitable modifications may be made thereto by individuals skilled in the art, which nonetheless remain within the scope of the invention. For example, the invention shall not be limited to any size or shape parameters, analytical equipment, hardware, and other similar items. In this regard, the present invention shall only be construed in accordance with the following claims:

The invention claimed is:

1. A sampling device for estimating simultaneously the magnitude of fluid fluxes and target chemical mass fluxes within a non-porous fluid flow systems comprising,
   a self contained shell that is inserted into a non-porous flow field containing a flowing fluid, where the shell contains a bundle of one or more permeable sorptive columns positioned to hydraulically connect to the fluid in the flow field surrounding shell through surface ports and conduit, the sorptive columns are packed with at least one insoluble sorptive matrix that is preloaded with a known mass of at least one resident tracer, wherein the sorbent matrix has the capacity to selectively adsorb, absorb or otherwise retain target chemical present in the flowing fluid.

2. The sampling device of claim 1 wherein the shell is formed in the shape of a hydrofoil.

3. A method of estimating simultaneously the magnitude of cumulative and time-average fluid fluxes and target chemical mass fluxes within a non-porous fluid flow systems comprising,
   a. providing at least one permeable sorptive column containing at least one insoluble sorbent matrix and at least one resident tracer of known mass sorbed on the sorbent;

b. providing a shell having surface ports, at least two pressure transducers and at least one chemical sensor, where the shell is shaped to cause a pressure differential when located in a fluid flow system, where the pressure transducers are located on or in the shell to measure the pressure differential and where the chemical sensor determines the instantaneous chemical composition and concentration of a target chemical in the fluid flow system;

c. positioning a bundle of one or more of the sorptive columns inside or outside the shell so that the surface ports can be hydraulically connected to the bundle of sorptive columns and to a flow field containing a fluid flux outside the shell;

d. inserting the shell into a non-porous flow system having fluid flux;

e. monitoring the pressure differential detected by the pressure transducers; and f. determining the chemical composition and concentration of a target chemical using the chemical sensor;

g. allowing fluid in the fluid flux to enter the sorptive columns passively through the surface ports;

h. allowing the fluid to contact the sorbent matrix; recording the time that the sorbent matrix is in contact with the fluid from the flow field;

j. removing the sorptive columns from the hydrofoil;

k. visually determining tracer displacement in the sorbent matrix if dyes are used or, if tracers are not visually detectable, analyzing the sorbent matrix for the mass of resident tracer remaining on the sorbent matrix to quantify a cumulative fluid flux; and l. determining the mass of the target chemical retained on the sorbent matrix to quantify a solute mass flux.

* * * * *

UNITED STATES PATENT AND TRADEMARK OFFICE
CERTIFICATE OF CORRECTION

PATENT NO. : 7,284,448 B2 Page 1 of 1
APPLICATION NO. : 10/989617
DATED : October 23, 2007
INVENTOR(S) : Harald Rene Klammler et al.

It is certified that error appears in the above-identified patent and that said Letters Patent is hereby corrected as shown below:

Column 10, line 31, please delete "$0 \leqq \alpha_c \leqq 2\text{Л}$" and add -- $0 \leq \alpha_c \leq 2\text{Л}$ --

Column 10, line 36, please delete "defined" and add -- defined as --

Column 10, line 59, please delete "X" and add -- $x$ --

Column 10, line 59, please delete "$x_j$" and add -- $x_j$ --

Column 14, line 5, please delete "recording the time that the sorbent matrix is in contact with the fluid from the flow field;"

Column 14, line 6, please add -- i. recording the time that the sorbent matrix is in contact with the fluid from the flow field; --

Signed and Sealed this

Twenty-seventh Day of May, 2008

JON W. DUDAS
*Director of the United States Patent and Trademark Office*